(12) United States Patent
Abe et al.

(10) Patent No.: US 12,396,471 B2
(45) Date of Patent: Aug. 26, 2025

(54) COMPOSITION CONTAINING SESAMIN AND PQQ

(71) Applicant: SUNTORY HOLDINGS LIMITED, Osaka (JP)

(72) Inventors: Chie Abe, Kyoto (JP); Yuki Yagita, Kyoto (JP); Yoshiko Ono, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 596 days.

(21) Appl. No.: 17/788,514

(22) PCT Filed: Dec. 18, 2020

(86) PCT No.: PCT/JP2020/047425
§ 371 (c)(1),
(2) Date: Jun. 23, 2022

(87) PCT Pub. No.: WO2021/132077
PCT Pub. Date: Jul. 1, 2021

(65) Prior Publication Data
US 2023/0040209 A1 Feb. 9, 2023

(30) Foreign Application Priority Data
Dec. 27, 2019 (JP) ................. 2019-238782

(51) Int. Cl.
*A23L 33/135* (2016.01)
*A23L 33/105* (2016.01)
(Continued)

(52) U.S. Cl.
CPC ........... *A23L 33/135* (2016.08); *A23L 33/105* (2016.08); *A61K 31/36* (2013.01);
(Continued)

(58) Field of Classification Search
None
See application file for complete search history.

(56) References Cited

U.S. PATENT DOCUMENTS

2007/0259908 A1 11/2007 Fujii et al.
2010/0048695 A1 2/2010 Ono et al.
(Continued)

FOREIGN PATENT DOCUMENTS

CN 101264076 A 9/2008
CN 101801370 A 8/2010
(Continued)

OTHER PUBLICATIONS

Umeda-Sawada, Rumi; et al; "Effect of Sesamin on Mitochondrial and Peroxisomal B-Oxidation of Arachidonic and Eicosapentaenoic Acids in Rat Liver" Lipids, 36, 483-489, 2001 (Year: 2001).*
(Continued)

*Primary Examiner* — David W Berke-Schlessel
(74) *Attorney, Agent, or Firm* — WHDA, LLP

(57) ABSTRACT

The present invention aims to provide a highly safe composition that can be used for improving or maintaining mitochondrial function and/or mitochondrial energy production capacity or reducing a decline in mitochondrial function and/or mitochondrial energy production capacity and that allows easy intake and continuous ingestion without risk of side effects. The present invention also aims to provide, for example a method of improving or maintaining mitochondrial function and/or mitochondrial energy production capacity or reducing a decline in mitochondrial function and/or mitochondrial energy production capacity. The present invention relates to, for example, a composition containing at least one sesamin-class compound and pyrroloquinoline quinone (PQQ) or a salt thereof.

11 Claims, 1 Drawing Sheet

(51) Int. Cl.
| A61K 31/36 | (2006.01) |
| A61K 31/4745 | (2006.01) |
| A61P 43/00 | (2006.01) |
| C12N 9/02 | (2006.01) |

(52) U.S. Cl.
CPC .......... *A61K 31/4745* (2013.01); *A61P 43/00* (2018.01); *C12N 9/0008* (2013.01); *C12Y 102/99003* (2013.01)

(56) References Cited

U.S. PATENT DOCUMENTS

| 2010/0061969 A1 | 3/2010 | Otsubo et al. |
| 2010/0261785 A1 | 10/2010 | Takemoto et al. |
| 2017/0312200 A1 | 11/2017 | Saeki |
| 2019/0269598 A1 | 9/2019 | Yabusaki |

FOREIGN PATENT DOCUMENTS

| CN | 105995350 A | 10/2016 |
| CN | 107106430 A | 8/2017 |
| JP | 2009-215170 A | 9/2009 |
| JP | 2012-019739 A | 2/2012 |
| JP | 2015-096494 A | 5/2015 |
| JP | 2017-141199 A | 8/2017 |
| JP | 2019-026582 A | 2/2019 |
| WO | 2006025247 A1 | 3/2006 |
| WO | 2018/079717 A1 | 5/2018 |

OTHER PUBLICATIONS

Maharjan, Sunita; et al; "Screening of dietary antioxidants against mitochondria-mediated oxidative stress by visualization of intracellular redox state" Bioscience, Biotechnology, and Biochemistry, 80, 726-734, 2016 (Year: 2016).*

Michailidis et al, "Recovery of Sesamin, Sesamolin, and Minor Lignans From Sesame Oil Using Solid Support-Free Liquid-Liquid Extraction and Chromatography Techniques and Evaluation of Their Enzymatic Inhibition Properties" Frontiers in Pharmacology, Jun. 2019, vol. 10, Article 723, pp. 1-13, cited in SG Search Report and Written Opinion dated Jul. 12, 2024. (13 pages).

Kumazawa et al, "Levels of pyrroloquinoline quinone in various foods", Biochem. J., 1995, vol. 307, pp. 331-333, cited in SG Search Report and Written Opinion dated Jul. 12, 2024. (3 pages).

Cookpad Natto Chinese-Style, Apr. 19, 2011, (retrieved from the Internet on Jan. 18, 2021), Document 1 in ISA opinion. (3 pages) cited in ISR.

It's Really Good! Natto Nutrients, May 14, 2016, (retrieved from the Internet on Jan. 18, 2021), Document 2 in ISA opinion. (7 pages); cited in ISR.

For People Who Suffer from Fatigue, Dec. 12, 2012, (retrieved from the Internet on Jan. 19, 2021), Document 3 in ISA opinion. (3 pages) cited in ISR.

Conley, Kevin et al.; Oxidative capacity and ageing in human muscle, The Journal of Physiology, 2000, vol. 526.1 pp. 203-210. (8 pages). cited in specification.

Chowanadisai et al.; Pyrroloquinoline Quinone Stimulates Mitochondrial Biogenesis through cAMP Response Element-binding Protein Phosphorylation and Increased PGC-1alpha Expression, Journal of Biological Chemistry, vol. 285, No. 1, pp. 142-152 Jan. 1, 2010 (11 pages) cited in specification.

Maharjan, Sunita et al.; Mitochondrial impairment triggers cytosolic oxidative stress and cell death following proteasome inhibition, Scientific Reports 4, 2014, pp. 1-11. (11 pages) cited in specification.

Kudryavtseva et al.; Mitochondrial dysfunction and oxidative stress in aging and cancer, Oncotarget, vol. 7, No. 29, 2016, pp. 44879-44905. (27 pages). cited in specification.

Takada, Shingo et al.; Sesami prevents the decline in exercise capacity and impairment of skeletal muscle mitochondrial function in mice with high-fat diet-induced diabetes, Experimental physiology, 2015, pp. 1319-1330. (12 pages) cited in specification.

International Preliminary Report on Patentabiilty and English translation of Written Opinion dated Feb. 2, 2021 issued in counterpart application No. PCT/JP22020/047425. (5 pages).

Chinese style natto, Cookpad, Apr. 19, 2011, retrieveed from https://cookpad.com/jp/recipes/19133767, pp. 1-3, cited in TW Office Action dated Oct. 28, 2024. (5 pages).

M. Murray, "Pyrroloquinoline quinone (PQQ): the next essential nutrient and supplement superstar", Nutrafoods, 2018, pp. 125-129, cited in TW Office Action dated Oct. 28, 2024. (5 pages).

* cited by examiner

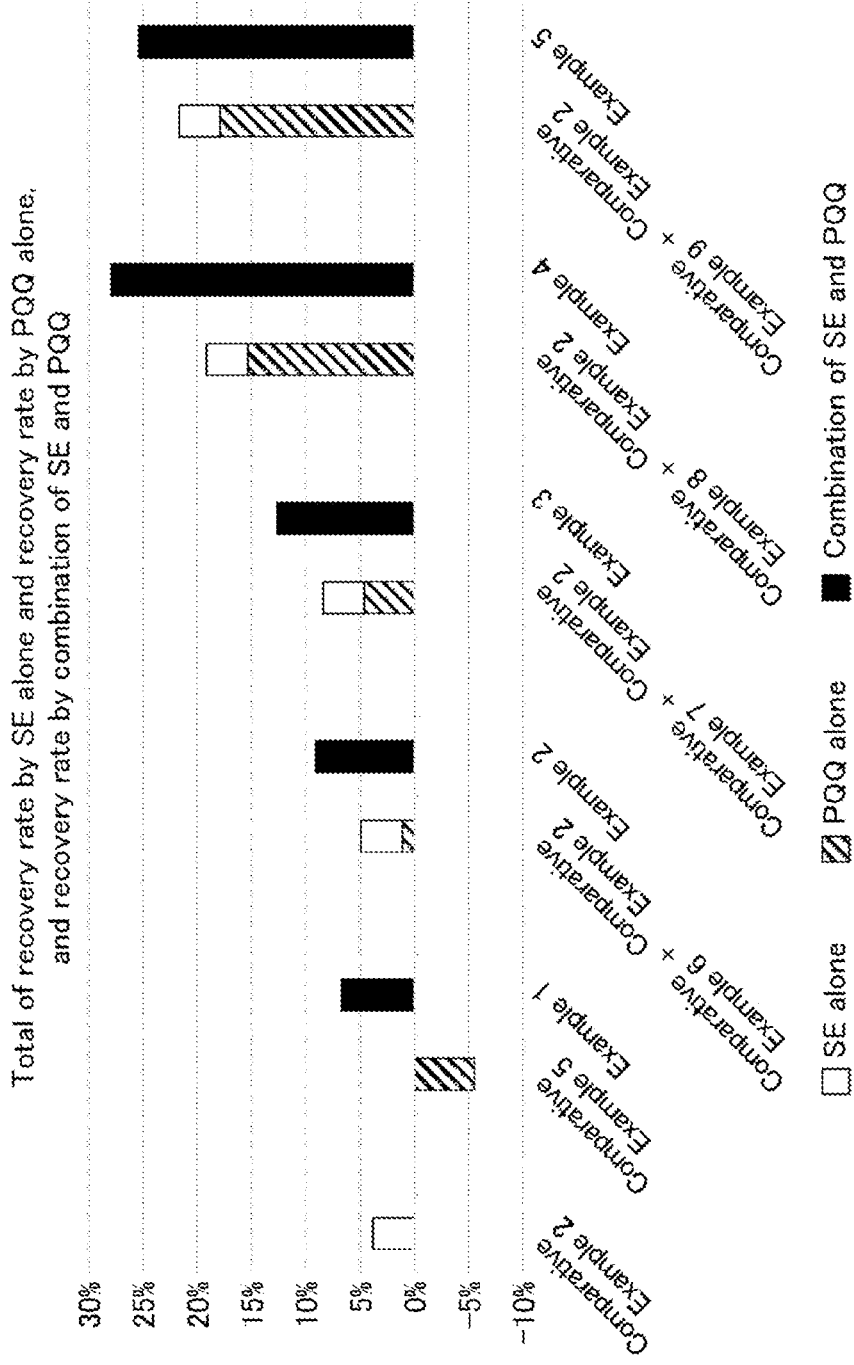

COMPOSITION CONTAINING SESAMIN AND PQQ

TECHNICAL FIELD

The present invention relates to a composition containing a sesamin-class compound and pyrroloquinoline quinone (PQQ). The present invention also relates to, for example, a method of improving or maintaining mitochondrial function and/or mitochondrial energy production capacity or reducing a decline in mitochondrial function and/or mitochondrial energy production capacity.

BACKGROUND ART

Energy production means production of energy required to maintain life activities.

Most of the energy is produced in mitochondria that are a type of organelles. Sugar, lipids, amino acids, and other nutrition sources taken from food are metabolized by glycolysis, pentose phosphate pathway, and citric acid pathway and converted into nicotinamide adenine dinucleotide (NADH). Then, NADH electrons are transferred to protein in mitochondrial respiratory chains (electron transport chains), and energy is produced in the form of adenosine triphosphate (ATP).

A decline in the amount of ATP production is known to cause various problems such as an increase in risk of developing obesity and diabetes due to reduced metabolic capacity, muscle strength decline, increase in fatigue, lethargy/decline in concentration, and depression.

Maintaining the amount of ATP production is important in fatigue alleviation, maintenance of concentration, exercise using muscle, and maintenance of vitality of mind and body.

Various agents for increasing energy production have been known which contain substrates required for ATP production such as carbohydrates, amino acids, and lipids (Patent Literature 1).

As described above, the substrates required for ATP production are converted into ATP via mitochondrial electron transport chains. However, mitochondrial function decline prevents production of ATP, even if there are more substrates.

It is known that mitochondrial function decline is caused by aging and oxidative stress and results in a decline in the amount of ATP production (Non-Patent Literatures 1 and 4).

In the case of ingestion of an ingredient as a supplement that reduces a decline in mitochondrial function, a form that allows easy intake by consumers for continuous ingestion is desirable. In particular, in the case of elderly people, small tablets and small capsules are desirable because swallowing function declines with aging. A supplement tends to be bulky particularly when it contains multiple ingredients, so that it is desirable to use an ingredient that is highly effective even when used in a small amount or a combination of such ingredients in order to reduce the volume of a tablet or capsule.

Here, sesamin is a lignan compound found in sesame and has been reported as having an antioxidant effect. According to a report using a diabetic mouse model, sesamin has an action that reduces a decline in mitochondrial function by an antioxidant effect (Non-Patent Literature 5). Sesamin is also known to exert, based on its antioxidant effect, an action that reduces mitochondrial active oxygen production and an action that reduces mitochondrial membrane potential drop (Non-Patent Literature 2). According to another report, sesamin activates PGC1α involved in mitochondrial biogenesis (Patent Literature 2).

It has also been reported that pyrroloquinoline quinone (PQQ) has an action that activates mitochondrial function via PGC1α (Non-Patent Literature 3).

CITATION LIST

Patent Literature

Patent Literature 1: JP 2009-215170 A
Patent Literature 2: WO 2018/079717

Non-Patent Literature

Non-Patent Literature 1: Conley, Kevin E., Sharon A. Jubrias, and Peter C. Esselman, "Oxidative capacity and ageing in human muscle", The Journal of Physiology 526.1 (2000): 203-210.
Non-Patent Literature 2: Maharjan, Sunita, et al., "Mitochondrial impairment triggers cytosolic oxidative stress and cell death following proteasome inhibition", Scientific Reports 4 (2014): 5896.
Non-Patent Literature 3: Chowanadisai, Winyoo, et al., "Pyrroloquinoline quinone stimulates mitochondrial biogenesis through cAMP response element-binding protein phosphorylation and increased PGC-1α expression", Journal of Biological Chemistry 285.1 (2010): 142-152.
Non-Patent Literature 4: Kudryavtseva, Anna V., et al., "Mitochondrial dysfunction and oxidative stress in aging and cancer", Oncotarget 7.29 (2016): 44879.
Non-Patent Literature 5: Takada, Shingo, et al., "Sesamin prevents decline in exercise capacity and impairment of skeletal muscle mitochondrial function in mice with high-fat diet-induced diabetes", Experimental Physiology 100.11 (2015): 1319-1330.

SUMMARY OF INVENTION

Technical Problem

Energy is constantly required to maintain life activities, so that there is a desire for a highly safe method of promoting production of energy that can be taken in continuously without risk of side effects. There has been suggested a method of increasing the amount of energy production by ingestion of substrates of energy production, however, its effect is limited in a state of mitochondrial function decline. While some food ingredients are known to have an action that improves energy production, it is desirable to use an ingredient that exerts its effect even when used in a small amount or to use a combination of such ingredients in terms of easy intake and safety for continuous ingestion.

The present invention aims to provide a highly safe composition that can be used for improving or maintaining mitochondrial function and/or mitochondrial energy production capacity or reducing a decline in mitochondrial function and/or mitochondrial energy production capacity and that allows easy intake and continuous ingestion without risk of side effects. The present invention also aims to provide, for example a method of improving or maintaining mitochondrial function and/or mitochondrial energy production capacity or reducing a decline in mitochondrial function and/or mitochondrial energy production capacity.

Solution to Problem

The present inventors conducted extensive studies to solve the problems described above. They considered that it is effective, as a means that allows easy intake and continuous ingestion, to allow an ingredient to exert its effect even when used in a small amount, and studied ingredients that can be used for improving or maintaining mitochondrial function and/or mitochondrial energy production capacity or reducing a decline in mitochondrial function and/or mitochondrial energy production capacity. As a result, the present inventors found that when a sesamin-class compound as a component that maintains and activates mitochondrial function is combined with pyrroloquinoline quinone (PQQ) or a salt thereof as a compound that activates mitochondrial function, the resulting combination improves or maintains mitochondrial function and/or mitochondrial energy production capacity or reduces a decline in mitochondrial function and/or mitochondrial energy production capacity in a more effective (synergistic) manner than when sesamin alone or pyrroloquinoline or its salt alone is used for treatment. Thus, the present invention was completed.

The present invention relates to the following composition.

(1) A composition containing at least one sesamin-class compound and pyrroloquinoline quinone (PQQ) or a salt thereof.

(2) The composition according to (1) above, wherein the at least one sesamin-class compound includes at least one of sesamin or episesamin.

(3) The composition according to (1) or (2) above, wherein a weight ratio of the PQQ or a salt thereof to the sesamin-class compound (PQQ or a salt thereof/sesamin-class compound) in PQQ equivalent is 0.01 to 100.

(4) The composition according to any one of (1) to (3) above, wherein the composition improves or maintains mitochondrial function or reduces a decline in mitochondrial function.

(5) The composition according to any one of (1) to (4) above, wherein the composition improves or maintains mitochondrial energy production capacity or reduces a decline in mitochondrial energy production capacity.

(6) The composition according to any one of (1) to (5) above, wherein the composition is for use in improving or maintaining vitality or reducing a decline in vitality.

(7) The composition according to any one of (1) to (6) above, wherein the composition is an anti-fatigue composition.

(8) The composition according to any one of (1) to (7) above, wherein the composition is an oral composition.

(9) The composition according to any one of (1) to (8) above, wherein the composition is a food or beverage.

(10) The composition according to any one of (1) to (9) above, wherein the composition is labeled with at least one function claim selected from the group consisting of "alleviating feelings of fatigue", "being less susceptible to fatigue", "maintaining vitality", "improving vitality", "facilitating energy production", and "being full of energy".

(11) A method of improving or maintaining at least one of mitochondrial function or mitochondrial energy production capacity or reducing a decline in at least one of mitochondrial function or mitochondrial energy production capacity, the method including administering at least one sesamin-class compound and pyrroloquinoline quinone (PQQ) or a salt thereof.

(12) A method of reducing, alleviating, or ameliorating fatigue, the method including administering at least one sesamin-class compound and pyrroloquinoline quinone (PQQ) or a salt thereof.

(13) Use of at least one sesamin-class compound and pyrroloquinoline quinone (PQQ) or a salt thereof for improving or maintaining at least one of mitochondrial function or mitochondrial energy production capacity or reducing a decline in at least one of mitochondrial function or mitochondrial energy production capacity.

(14) Use of at least one sesamin-class compound and pyrroloquinoline quinone (PQQ) or a salt thereof for anti-fatigue.

Advantageous Effects of Invention

The present invention can provide a highly safe composition that can be used for improving or maintaining mitochondrial function and/or mitochondrial energy production capacity or reducing a decline in mitochondrial function and/or mitochondrial energy production capacity and that allows easy intake and continuous ingestion without risk of side effects. With ingestion of the composition of the present invention, an action that improves mitochondrial function and/or mitochondrial energy production capacity, an action that maintains mitochondrial function and/or mitochondrial energy production capacity, or an action that reduces a decline in mitochondrial function and/or mitochondrial energy production capacity can be exerted effectively without risk of side effects, which results in an anti-fatigue effect. The present invention can also provide, for example a method of improving or maintaining mitochondrial function and/or mitochondrial energy production capacity or reducing a decline in mitochondrial function and/or mitochondrial energy production capacity.

BRIEF DESCRIPTION OF DRAWINGS

FIG. 1 is a graph showing effects on the amount of ATP production by a composition containing a 100 nM sesamin-episesamin mixture (SE) (sesamin:episesamin (weight ratio=1:1)) (Comparative Example 2), compositions containing PQQ (Comparative Examples 5 to 9), and compositions containing 100 nM SE and PQQ (Examples 1 to 5).

DESCRIPTION OF EMBODIMENTS

The composition of the present invention contains at least one sesamin-class compound.

The sesamin-class compound is one of main lignan-class compounds of sesame, and is contained in an amount of about 0.5 to 1.0 wt % in sesame. While long-term ingestion of artificially synthesized compounds is not preferred in terms of unexpected side effects and the like, the sesamin-class compound whose safety is guaranteed is best suited for long-term ingestion.

(Sesamin-Class Compound)

In the present invention, the term "the sesamin-class compound" is a collective term for compounds including sesamin and its analogs. Sesamin is one of main lignan compounds found in sesame. Examples of the sesamin analogs include episesamin and dioxabicyclo[3.3.0]octane derivatives described in JP H04-9331 A. The at least one sesamin-class compound may include a single compound alone or two or more of these compounds above. Specific examples of the sesamin-class compound include sesamin, episesamin, sesaminol, episesaminol, sesamol, and sesamolin. Stereoisomers or racemates of these compounds may be used alone or in mixture. In addition, metabolites of the sesamin-class compound (e.g., those described in JP 2001-139579 A) are also sesamin analogs included in the sesamin-class compound of the present invention, and can also be used in the present invention, as long as they exhibit the effect(s) of the present invention. In the present invention, sesamin and/or episesamin can be suitably used as the at least one sesamin-class compound. Sesamin and episesamin can be more suitably used. When sesamin and episesamin are used, the ratio of these components is not limited. For example, the ratio of sesamin to episesamin by weight is preferably 1:0.1 to 1:9, more preferably 1:0.3 to 1:3, still more preferably 1:0.5 to 1:2.

The sesamin-class compound for use in the present invention is not limited in any way by its form, production method, or the like. For example, when the sesamin-class compound is sesamin, sesamin extracted from sesame oil by a known method (e.g., the method described in JP H04-9331 A) can be used (hereinafter, such sesamin is called a sesamin extract or purified sesamin). Commercially available sesame oil (in liquid form) can also be used as is. However, when sesame oil is used, the characteristic flavor of sesame oil is sometimes evaluated as being organoleptically undesirable. Thus, a tasteless and odorless sesamin extract (or purified sesamin) from sesame oil is preferably used. In addition, since sesame oil has a low sesamin content, use of sesame oil to incorporate a desirable amount of sesamin results in excess volume per unit dose of a composition to be prescribed. This sometimes causes inconvenience in ingestion. In particular, in the case where the composition is formulated for oral administration, the preparation (e.g., tablet or capsule) becomes so bulky that it causes trouble in ingestion. Thus, use of sesamin extract (or purified sesamin) from sesame oil is preferred because it does not require a large amount of ingestion. The sesamin-class compound can also be obtained by synthesis. For example, sesamin and episesamin can be synthesized by the method of Beroza et al. (J. Am. Chem. Soc., 78, 1242 (1956)). Metabolites of sesamin and episesamin can be synthesized by the method of Urata et al. (Chem. Pharm. Bull. (Tokyo), 56(11), 1611-2 (2008)).

The sesamin-class compound is found in natural products and food and beverages. It is a compound with a long history of consumption and recognized high levels of safety. Long-term ingestion of artificially synthesized compounds is not preferred in terms of unexpected side effects and the like. In contrast, a sesamin-class compound whose safety is guaranteed is best suited for continuous ingestion and long-term ingestion.

(Pyrroloquinoline Quinone (PQQ))

The composition of the present invention contains pyrroloquinoline quinone (PQQ) or a salt thereof.

The PQQ is a redox coenzyme. The PQQ or a salt thereof is found in various organisms including plants, bacteria, and animals, and thus can be prepared by extraction from various organisms. Commercially available PQQ or a salt thereof can also be used. In the present invention, the composition of the present invention may contain a raw material derived from plants rich in PQQ or a salt thereof, for example, as long as the effect(s) of the present invention is achieved.

The salt of PQQ is preferably a salt that can be used in a food or beverage, pharmaceutical product, or the like. Examples include alkali metal salts such as a sodium salt and a potassium salt, and alkaline earth metal salts such as a calcium salt and a magnesium salt. Specifically, the salt of PQQ that can be used include, for example, one or more selected from phosphates, hydrochlorides, sulfates, acetates, and the like of magnesium, manganese, calcium, sodium, potassium, copper, iron, zinc, and the like. The salt is preferably a sodium salt.

The number of substituted atoms in the salt of PQQ is 1 to 3, preferably 2. Preferably, the salt of PQQ is a disodium salt of PQQ.

PQQ is found in various kinds of food. For example, it is found in fermented food such as natto, tofu, and fermented soybean paste; vegetables such as parsley, peppers, and spinach; and fruits such as kiwi fruits and papaya. Long-term ingestion of artificially synthesized compounds is not preferred in terms of unexpected side effects and the like. In contrast, PQQ whose safety is guaranteed is best suited for continuous ingestion and long-term ingestion.

(Composition containing a Sesamin-Class Compound and PQQ or a Salt Thereof)

The composition of the present invention contains the sesamin-class compound and the PQQ or a salt thereof. In order for these components to synergistically improve the action that improves mitochondrial function and/or mitochondrial energy production capacity, the action that maintains mitochondrial function and/or mitochondrial energy production capacity, or the action that reduces a decline in mitochondrial function and/or mitochondrial energy production capacity, the weight ratio of the PQQ to the sesamin-class compound (PQQ/sesamin-class compound) in PQQ equivalent in the composition of the present invention is preferably 0.01 to 100, more preferably 0.1 to 10, still more preferably 0.2 to 5. The anti-fatigue effect is achieved by improving the action that improves mitochondrial function and/or mitochondrial energy production capacity, the action that maintains mitochondrial function and/or mitochondrial energy production capacity, or the action that reduces a decline in mitochondrial function and/or mitochondrial energy production capacity. Thus, setting the weight ratio of the PQQ or a salt thereof to the sesamin-class compound in the specific range described above in the composition of the present invention is also preferred in terms of anti-fatigue action.

Herein, the amount of PQQ or a salt thereof is converted to a value equivalent to the amount of pyrroloquinoline quinone (PQQ).

The sesamin-class compound and the PQQ or a salt thereof contained in the composition of the present invention can synergistically improve the action that improves mitochondrial function and/or mitochondrial energy production capacity, the action that maintains mitochondrial function and/or mitochondrial energy production capacity, and the action that reduces a decline in mitochondrial function and/or mitochondrial energy production capacity. Thus, the above actions can be exerted with the use of the composition of the present invention even when the amount thereof is small. A reduction in dose leads to easy intake, resulting in a composition suitable for continuous ingestion.

The composition of the present invention can improve or maintain mitochondrial function or reduce a decline in mitochondrial function. The composition of the present invention can also improve or maintain mitochondrial energy production capacity or reduce a decline in mitochondrial energy production capacity. Thus, the composition of the present invention achieves an anti-fatigue effect.

Herein, the mitochondrial function and mitochondrial energy production capacity only need to be evaluated based on common knowledge in the technical field to which the present invention belongs to. Any method may be used for evaluation. For example, the mitochondrial function can be evaluated by continuously evaluating the oxygen consumption rate (hereinafter also described as "OCR") of mitochondria during ATP synthesis in cells as the measurement target, using an extracellular flux analyzer, while adding ATP synthase inhibitors (e.g., oligomycin and rotenone) and an uncoupler (e.g., carbonyl cyanide-p-trifluoromethoxy phenylhydrazone (FCCP)) thereto. Evaluation items may be, for example, basal respiration, ATP production capacity, and maximal respiration, which are considered to be major indices for evaluation of mitochondrial function. The mitochondrial function can be evaluated by analyzing these evaluation items.

The composition of the present invention can be provided as an anti-fatigue composition. Hereinafter, the term "the composition of the present invention" encompasses the anti-fatigue composition. Herein, the term "fatigue" means a temporary decline in physical activity ability and mental vitality due to physical or mental causes. Fatigue is usually associated with feelings of fatigue (e.g., discomfort and reduced motivation for activities) and the like. The term "anti-fatigue" refers to reduce, alleviate, or ameliorate fatigue. The term "reducing fatigue" encompasses increasing resistance to fatigue, preventing fatigue (including reducing risks in a subject at risk of fatigue), and the like. The term "alleviating fatigue" encompasses alleviating fatigue symptoms (e.g., feelings of fatigue) and the like. The term "ameliorating fatigue" encompasses helping recovery from fatigue, ameliorating fatigue symptoms, and the like.

The anti-fatigue composition of the present invention can be used, for example, to reduce, alleviate, or ameliorate physical fatigue and/or mental fatigue, and to reduce, alleviate, or ameliorate feelings of physical fatigue and/or feelings of mental fatigue. In particular, the anti-fatigue composition can be preferably used to reduce, alleviate, or ameliorate physical fatigue, and to reduce, alleviate, or ameliorate feelings of physical fatigue.

The composition of the present invention can be provided in the form of a food or beverage, a pharmaceutical product, a quasi-pharmaceutical product, feed, or the like. The composition of the present invention may be a food or beverage, a pharmaceutical product, a quasi-pharmaceutical product, feed, or the like by itself for improving or maintaining mitochondrial function or reducing a decline in mitochondrial function or for improving or maintaining mitochondrial energy production capacity or reducing a decline in mitochondrial energy production capacity, or may be a material, a preparation, or the like that is added thereto.

For example, the composition of the present invention may be provided as an agent or the like, but it is not limited thereto. The agent can be directly provided as a composition, or can be provided as a composition containing the agent. In one embodiment of the present invention, the anti-fatigue composition of the present invention can be regarded as an anti-fatigue agent.

The composition of the present invention may be an oral composition or a parenteral composition, preferably an oral composition. The oral composition may be a food or beverage, an oral pharmaceutical product, an oral quasi-pharmaceutical product, or feed, preferably a food or beverage or an oral pharmaceutical product, more preferably a food or beverage.

The composition of the present invention may contain optional additives and optional components, in addition to the at least one sesamin-class compound and the PQQ or a salt thereof, as long as the effect(s) of the present invention is not impaired. Such additives and components can be selected according to the composition form or the like. Those that can be used generally in foods, beverages, pharmaceutical products, quasi-pharmaceutical products, feed, and the like can be used. When the composition of the present invention is provided as a food or beverage, a pharmaceutical product, a quasi-pharmaceutical product, feed, or the like, any common method can be used for production.

For example, when the composition of the present invention is provided as a food or beverage, a component usable in food or beverages (e.g., a food material or an optional food additive) can be added to the at least one sesamin-class compound and the PQQ or a salt thereof to provide various types of foods or beverages. Non-limiting examples of the foods or beverages include general foods and beverages, health foods, health beverages, foods with function claims, foods for specified health uses, dietary supplements, and foods and beverages for the sick. The health foods, the foods with function claims, the foods for specified health uses, dietary supplements, and the like can be used, for example, in various forms of preparations such as fine granules, tablets, granules, powders, capsules, chewable tablets, dry syrups, syrups, liquids, beverages, and liquid foods.

When the composition of the present invention is provided as a pharmaceutical product or a quasi-pharmaceutical product, for example, a pharmacologically acceptable carrier, an optional additive, or the like can be added to the at least one sesamin-class compound and the PQQ or a salt thereof to provide various dosage forms of pharmaceutical products or quasi-pharmaceutical products. Such a carrier, an additive, or the like may be any pharmacologically acceptable one that can be used in pharmaceutical products or quasi-pharmaceutical products. Examples thereof include excipients, binders, disintegrants, lubricants, antioxidants, and colorants. One or more of these can be used. The form of administration (ingestion) of the pharmaceutical product or quasi-pharmaceutical product may be an oral or parenteral (transdermal, transmucosal, or enteral administration, injection, or the like). When the composition of the present invention is provided as a pharmaceutical product or a quasi-pharmaceutical product, it is preferably an oral pharmaceutical product or an oral quasi-pharmaceutical product. Examples of the dosage forms of preparations for oral administration include liquids, tablets, powders, fine granules, granules, sugar-coated tablets, capsules, suspensions, emulsions, and chewable tablets. The pharmaceutical product may be for non-human animals.

When the composition of the present invention is provided as feed, the at least one sesamin-class compound and the PQQ or a salt thereof are simply added to feed. The feed includes feed additives. Examples of the feed include livestock feed for animals such as cows, pigs, chickens, sheep, and horses; feed for small animals such as rabbits, rats, and mice; and pet food for animals such as dogs, cats, and birds.

The amount of sesamin-class compound in the composition of the present invention is not limited, and can be set according to the form of the composition of the like.

The total amount of sesamin-class compound in the composition of the present invention is, for example, preferably 0.001 wt % or more, more preferably 0.01 wt % or more, still more preferably 0.05 wt % or more and is preferably 10 wt % or less, more preferably 5 wt % or less.

In one embodiment, the total amount of sesamin-class compound in the composition is preferably 0.001 to 10 wt %, more preferably 0.01 to 5 wt %, still more preferably 0.05 to 5 wt %.

The amount of PQQ or a salt thereof in the composition of the present invention is not limited, and can be set according to its form or the like.

The amount of PQQ or a salt thereof in the composition of the present invention is, for example, preferably 0.0001 wt % or more, more preferably 0.001 wt % or more, still more preferably 0.005 wt % or more, and is preferably 20 wt % or less, more preferably 10 wt % or less.

In one embodiment, the amount of PQQ or a salt thereof in PQQ equivalent in the composition is preferably 0.0001 to 20 wt %, more preferably 0.001 to 10 wt %, still more preferably 0.05 to 10 wt %.

Preferably, the composition of the present invention is orally ingested (orally administered). The dose (intake) of the composition of the present invention is not limited. The dose of the composition of the present invention may be any amount that produces an effect of improving or maintaining mitochondrial function or reducing a decline in mitochondrial function, an effect of improving or maintaining mitochondrial energy production capacity or reducing a decline in mitochondrial energy production capacity, and/or an anti-fatigue effect. The dose may be appropriately set according to the administration form, administration method, body weight of a subject, and the like.

In one embodiment, when a human (adult) is subjected to oral ingestion or administration of the composition of the present invention, the total dose of the sesamin-class compound is preferably 0.5 mg or more, more preferably 1 mg or more, still more preferably 3 mg or more, and is preferably 200 mg or less, more preferably 100 mg or less, still more preferably 80 mg or less per 60 kg body weight per day. The total dose of PQQ or a salt thereof in PQQ equivalent is preferably 0.5 mg or more, more preferably 1 mg or more, still more preferably 3 mg or more, and is preferably 200 mg or less, more preferably 100 mg or less, still more preferably 80 mg or less per 60 kg body weight per day.

In one embodiment, in the case of a human (adult), the total dose of the sesamin-class compound is preferably 0.5 to 200 mg, more preferably 1 to 100 mg, still more preferably 3 to 80 mg per 60 kg body weight per day. In the case of a human (adult), the total dose of PQQ or a salt thereof in PQQ equivalent is preferably 0.5 to 400 mg, more preferably 1 to 200 mg, still more preferably 3 to 160 mg per 60 kg body weight per day.

Preferably, the sesamin-class compound in the above amount and the PQQ or a salt thereof in the above amount are ingested or administered in one or more portions per day, for example, in one to several portions (e.g., two or three portions) per day.

In one embodiment, preferably, the sesamin-class compound and the PQQ or a salt thereof in the above amounts are orally ingested by or administered to a human.

In one embodiment, the composition of the present invention can be used to subject a human to ingestion or administration of the sesamin-class compound and the PQQ or a salt thereof in the above amounts per 60 kg body weight per day.

When the composition contains two or more sesamin-class compounds, the total dose of the sesamin-class compounds is the sum of these compounds.

In one embodiment, preferably, sesamin and/or episesamin is orally ingested by or administered to a human (adult) in an amount of preferably 0.5 to 200 mg, more preferably 1 to 100 mg, still more preferably 3 to 80 mg per 60 kg body weight per day as the total dose of sesamin and episesamin.

Preferably, the composition of the present invention is continuously ingested or administered. The above effect(s) is likely to be enhanced when the sesamin-class compound and the PQQ or a salt thereof are continuously ingested or administered. In one embodiment, the composition of the present invention is continuously ingested or administered for preferably one week or more, more preferably four weeks or more, still more preferably eight weeks or more, particularly preferably 12 weeks or more.

The subject (administration subject) subjected to ingestion or administration of the composition of the present invention is not limited. Humans and non-human animals can be subjected to ingestion. Examples of the non-human animals include industrial animals, pets, and laboratory animals. Specifically, the term "industrial animals" refers to animals that are bred for industrial purposes. Examples include farm animals such as cows, horses, pigs, goats, and sheep; poultry such as chickens, ducks, quals, turkeys, and ostriches; and fish such as yellowtail, young yellowtail, red seabream, Japanese horse mackerel, carp, rainbow trout, and eel. The term "pets" refers to pet animals or companion animals such as dogs, cats, common marmosets, birds, and hamsters. The term "laboratory animals" refers to mice, rats, guinea pigs, beagles, miniature pigs, rhesus monkeys, crab-eating monkeys, and other animals that are used in research in fields of medicine, biology, agronomy, pharmacy, and the like.

The administration subject of the composition of the present invention is preferably a human or non-human mammal, more preferably a human.

In one embodiment, the administration subject may be one needing or wanting to improve or maintain mitochondrial function or reduce a decline in mitochondrial function, one needing or wanting to improve or maintain mitochondrial energy production capacity or reduce a decline in mitochondrial energy production capacity, or one needing or wanting an anti-fatigue effect. As described above, aging is known to cause mitochondrial function decline. In one embodiment, the subject of the composition of the present invention may be a middle-aged or older person. The composition of the present invention may be an anti-fatigue composition for middle-aged and older people (preferably for elderly people). The composition of the present invention can also be used by healthy people, for example, for a purpose such as improvement or maintenance of mitochondrial function or reduction of a decline in mitochondrial function, improvement or maintenance of mitochondrial energy production capacity or reduction of a decline in mitochondrial energy production capacity, or an anti-fatigue effect.

The composition of the present invention may be labeled with at least one function claim selected from the group consisting of "alleviating feelings of fatigue", "being less susceptible to fatigue", "maintaining vitality", "improving vitality", "facilitating energy production", and "being full of energy". For example, the feelings of fatigue and the decline in vitality may be those to which one becomes more sensitive with aging. The energy production may be energy produced in cells or mitochondria. In one embodiment of the present invention, preferably, the composition of the present invention is a food or beverage labeled with one or more function claims described above. These labels may be labels indicating use for obtaining these functions.

The present invention encompasses the following uses and methods:

a method for improving or maintaining mitochondrial function and/or mitochondrial energy production capacity or reducing a decline in mitochondrial function and/or mitochondrial energy production capacity, the method including administering at least one sesamin-class compound and pyrroloquinoline quinone (PQQ) or a salt thereof;

a method of reducing, alleviating, or ameliorating fatigue, the method including administering at least one sesamin-class compound and pyrroloquinoline quinone (PQQ) or a salt thereof;

use of at least one sesamin-class compound and pyrroloquinoline quinone (PQQ) or a salt thereof for improving or maintaining mitochondrial function and/or mitochondrial energy production capacity or reducing a decline in mitochondrial function and/or mitochondrial energy production capacity; and use of at least one sesamin-class compound and pyrroloquinoline quinone (PQQ) or a salt thereof for anti-fatigue.

The above methods may be therapeutic or non-therapeutic. The above uses may be therapeutic or non-therapeutic.

Administration of at least one sesamin-class compound and PQQ or a salt thereof can improve or maintain mitochondrial function and/or mitochondrial energy production capacity or reduce a decline in mitochondrial function and/or mitochondrial energy production capacity, which can result in an anti-fatigue effect.

The present invention also encompasses use of at least one sesamin-class compound and PQQ or a salt thereof for producing the composition of the present invention.

Specifically, the present invention may provide use of a composition containing at least one sesamin-class compound and PQQ or a salt thereof for improving or maintaining mitochondrial function and/or mitochondrial energy production capacity or reducing a decline in mitochondrial function and/or mitochondrial energy production capacity.

The present invention may also provide use of a composition containing at least one sesamin-class compound and PQQ or a salt thereof for producing an anti-fatigue composition.

In the above uses, preferred embodiments of the sesamin-class compound and the PQQ or a salt thereof are as described above for the composition of the present invention. The at least one sesamin-class compound may include a single compound alone or two or more of these compounds above. A salt of PQQ may be used as the PQQ or a salt thereof. In the above uses, preferably, the at least one sesamin-class compound and the PQQ or a salt thereof are administered to (ingested by) a subject at least once a day, for example, one to several times (e.g., two to three times) a day. In the above uses, preferably, the at least one sesamin-class compound and the PQQ or a salt thereof are orally administered (ingested). The above uses are preferably for humans or non-human mammals, more preferably for humans.

The above uses only require use of the at least one sesamin-class compound and the PQQ or a salt thereof in amounts (effective amounts) that produce a desirable effect(s). Preferred dose, administration subjects, and the like of the sesamin-class compound and the PQQ or a salt thereof are as described above for the composition of the present invention. The sesamin-class compound and the PQQ or a salt thereof may be administered as is, or may be administered in the form of a composition containing the sesamin-class compound. For example, the composition of the present invention described above may be used.

In the above uses, substantially simultaneous intake of a composition containing a sesamin-class compound and a composition containing PQQ or a salt thereof that were separately prepared, or intake of one of these compositions and then the other composition while the effect of the former composition is still active can enhance the effect(s) by the composition containing at least one sesamin-class compound and PQQ or a salt thereof, which is(are) intended by the present invention (the action that improves or maintains mitochondrial function or reduces a decline in mitochondrial function, the action that improves or maintains mitochondrial energy production capacity or reduces a decline in mitochondrial energy production capacity, and/or the anti-fatigue action). Thus, for example, a kit containing a composition containing a sesamin-class compound and a composition containing PQQ or a salt thereof is also encompassed in the scope of the composition of the present invention.

EXAMPLES

The present invention is described in further detail below with reference to examples. The present invention is not limited to these examples.

Examples 1 to 5

Evaluation Test of Mitochondrial Function of 100 nM Sesamin-Episesamin Mixture (SE) (Sesamin:Episesamin (Weight Ratio=1:1)) and PQQ·2Na To examine mitochondrial function, TIG-3 cells at $5.5 \times 10^3$ cells/well were seeded onto cell culture plates, and cultured at 37° C. with $CO_2$ (5%) for 24 hours. After 24 hours of culturing, compositions each containing a sesamin-episesamin mixture and PQQ were added to the media in the wells at the respective concentrations shown in Table 1 below, and cultured for 24 hours. Subsequently, the media containing the sesamin-episesamin mixture and the PQQ were removed, and the cells in the wells were treated with media containing $H_2O_2$ (800 μM) for two hours. Subsequently, each medium was replaced with an analysis medium, and the oxygen consumption rate was analyzed using an analyzer (XF analyzer, Agilent Technologies Japan, Ltd.). After completion of analysis, the nuclei were stained with Hoechst, and the cells were photographed by a fluorescence microscope "BZ-x" (Keyence Corporation). The number of cells was counted by image analysis. The amount of ATP production was the amount of decrease in oxygen consumption rate by the ATP synthase inhibitor (oligomycin). Table 1 and FIG. 1 show the results obtained.

Reference Example 1

Evaluation Test of Mitochondrial Function of Untreated Group

To examine mitochondrial function, TIG-3 cells at $5.5 \times 10^3$ cells/well were seeded onto a dedicated plate, and cultured at 37° C. with $CO_2$ (5%) for 24 hours. The cells were further cultured for 26 hours without adding a sesamin-episesamin mixture and a composition containing PQQ to the medium 24 hours after the first culturing and without treating cells in the well with a medium containing $H_2O_2$ (800 μM) for two hours. Then, the oxygen consumption rate in Reference Example 1 was analyzed and the number of cells was counted as in Example 1, except for the differences described above. The amount of ATP production was also measured. Table 1 shows the results obtained.

Comparative Example 1

Evaluation Test of Mitochondrial Function of $H_2O_2$-Treated Group

To examine mitochondrial function, TIG-3 cells at $5.5 \times 10^3$ cells/well were seeded onto a dedicated plate, and cultured at 37° C. with $CO_2$ (5%) for 24 hours. The cells were further cultured for 24 hours without adding a sesamin-episesamin mixture and a composition containing PQQ to the medium 24 hours after the first culturing. Then, the oxygen consumption rate in Comparative Example 1 was analyzed and the number of cells was counted as in Example 1, except for the differences described above. The amount of ATP production was also measured. Table 1 shows the results obtained.

Comparative Examples 2 to 9

Evaluation Test of Mitochondrial Function of Sesamin-Episesamin Mixture (Sesamin:Episesamin (Weight Ratio=1:1)) or PQQ-2Na To examine mitochondrial function, TIG-3 cells at $5.5 \times 10^3$ cells/well were seeded onto a dedicated plate, and cultured at 37° C. with $CO_2$ (5%) for 24 hours. After 24 hours of culturing, a sesamin-episesamin mixture or PQQ was added to each medium in the wells at the corresponding concentration shown in Table 1 below, and cultured for 24 hours. Except what is described above, the oxygen consumption rate in each of Comparative Examples 2 to 9 was analyzed, and the number of cells was counted as in Example 1. The amount of ATP production was measured. Table 1 shows the results obtained.

total recovery rate in Comparative Example 2 and Comparative Example 8. "Comparative Example 9+Comparative Example 2" is the total recovery rate in Comparative Example 2 and Comparative Example 9. "Comparative Example 6+Comparative Example 2", "Comparative Example 7+Comparative Example 2", "Comparative Example 8+Comparative Example 2", and "Comparative Example 9+Comparative Example 2" show the recovery rates of the respective combinations of the sesamin-class compound and the PQQ predicted from the recovery rate of the sesamin-class compound alone (Comparative Example 2) and the PQQ alone (Comparative Example 6, 7, 8, or 9).

<Results>

As shown in Table 1, treatment with 800 μM $H_2O_2$ according to Comparative Example 1 resulted in a decline in the amount of ATP production by 48.1%, compared to the control group (Reference Example 1). Treatment with the PQQ (10 nM) according to Comparative Example 5 resulted in a decline in the amount of ATP production by 5.5%, compared to the $H_2O_2$-treated group according to Comparative Example 1. In contrast, treatment with the PPQ according to Comparative Examples 6, 7, 8, or 9 (30 nM, 100 nM, 300 nM, or 1 μM) resulted in an increase in the amount of ATP production by 1.1%, 4.6%, 15.3%, or 17.8%, respectively, in a PQQ dose-dependent manner, compared to the

TABLE 1

| | $H_2O_2$ (μM) | SE (nM) | PQQ · 2Na (nM) | Number of n | Measured value (pmol/min/ $10^3$ cells) | Standard error | Recovery rate (%) from Comparative Example 1 | Standard error |
|---|---|---|---|---|---|---|---|---|
| Reference Example 1 | — | — | — | 6 | 12.37 | 0.7 | — | — |
| Comparative Example 1 | 800 | — | — | 6 | 6.42 | 0.4 | 100.0 | 6.2 |
| Comparative Example 2 | 800 | 100 | — | 6 | 6.66 | 0.3 | 103.8 | 5.3 |
| Comparative Example 3 | 800 | 300 | — | 6 | 6.93 | 0.5 | 108.0 | 8.1 |
| Comparative Example 4 | 800 | 1000 | — | 5 | 6.96 | 0.4 | 108.5 | 5.9 |
| Comparative Example 5 | 800 | — | 10 | 3 | 6.06 | 0.4 | 94.5 | 6.0 |
| Comparative Example 6 | 800 | — | 30 | 3 | 6.49 | 0.7 | 101.1 | 11.2 |
| Comparative Example 7 | 800 | — | 100 | 2 | 6.71 | —[1] | 104.6 | —[1] |
| Comparative Example 8 | 800 | — | 300 | 3 | 7.40 | 1.1 | 115.3 | 16.8 |
| Comparative Example 9 | 800 | — | 1000 | 3 | 7.56 | 0.9 | 117.8 | 14.8 |
| Example 1 | 800 | 100 | 10 | 3 | 6.85 | 0.3 | 106.7 | 4.1 |
| Example 2 | 800 | 100 | 30 | 3 | 7.00 | 0.3 | 109.1 | 4.5 |
| Example 3 | 800 | 100 | 100 | 3 | 7.23 | 0.6 | 112.6 | 9.7 |
| Example 4 | 800 | 100 | 300 | 3 | 8.21 | 0.8 | 127.9† | 12.5 |
| Example 5 | 800 | 100 | 1000 | 3 | 8.04 | 0.6 | 125.3† | 8.8 |

†p < 0.1, vs. Comparative Example 1
[1]Standard error is not calculated because n = 2.

In Table 1, values in "Measured value" (pmol/min/$10^3$ cells) show the amount of ATP production (the amount of decrease in oxygen consumption rate by the ATP synthase inhibitor) determined above.

Values in "Recovery rate (%) from Comparative Example 1" are each obtained by dividing a measured value in one example or comparative example by the measured value of Comparative Example 1 and multiplying the resulting value with 100. A higher recovery rate means a larger amount of ATP production. FIG. 1 shows the recovery rate (%) determined for the examples and comparative examples (recovery rate relative to Comparative Example 1). In FIG. 1, "SE" indicates the sesamin-episesamin mixture.

In FIG. 1, "Comparative Example 6+Comparative Example 2" is the total recovery rate in Comparative Example 2 and Comparative Example 6. "Comparative Example 7+Comparative Example 2" is the total recovery rate in Comparative Example 2 and Comparative Example 7. "Comparative Example 8+Comparative Example 2" is the $H_2O_2$-treated group according to Comparative Example 1. This confirms the effect of reducing a decline in the amount of ATP production by treatment with the PQQ. Treatment with the sesamin-episesamin mixture (100 nM, 300 nM, or 1 μM) according to Comparative Example 2, 3, or 4 resulted in an increase in the amount of ATP production in a sesamin-episesamin mixture dose-dependent manner, compared to the $H_2O_2$-treated group according to Comparative Example 1. This confirmed an effect of reducing a decline in the amount of ATP production by treatment with the sesamin-episesamin mixture. Next, treatment with the composition containing a sesamin-episesamin mixture (100 nM) and PQQ (10 nM, 30 nM, 100 nM, 300 nM, or 1 μM) according to Example 1, 2, 3, 4, or 5 resulted in an increase in the amount of ATP production by 6.7%, 9.1%, 12.6%, 27.8%, or 25.3%, respectively, compared to the $H_2O_2$-treated group according to Comparative Example 1. As shown in FIG. 1, each of these values is greater than the total rate of increase in the amount of ATP production by the sesamin-episesamin mixture alone and the amount of ATP production by the PQQ alone. This confirms that it is not that the amount of ATP production was simply additively increased compared to the PQQ and the sesamin-episesamin mixture, but the amount of ATP production was synergistically increased by the sesamin-episesamin mixture and the composition containing PQQ. In other words, the composition containing a sesamin-episesamin mixture and PQQ was found to exert its effect even when used in a small amount because the composition exhibits a synergistic effect owing to the presence of both components therein.

The composition containing a sesamin-episesamin mixture and PQQ was also found to exhibit a synergistic effect on reducing a decline in the amount of ATP production.

The above clearly shows that the sesamin-episesamin mixture and the PQQ exhibit a synergistic effect of reducing a decline in the amount of ATP production. Thus, the composition containing one sesamin-class compound and PQQ or a salt thereof can improve or maintain mitochondrial function or reduce a decline in mitochondrial function, and can also maintain or improve mitochondrial energy production capacity or reduce a decline in mitochondrial energy production capacity. This results in an anti-fatigue effect.

The invention claimed is:

1. A composition comprising:
   at least one sesamin-class compound and pyrroloquinoline quinone (PQQ) or a salt thereof,
   wherein a weight ratio of the PQQ or a salt thereof to the sesamin-class compound (PQQ or a salt thereof/sesamin-class compound) in PQQ equivalent is 0.1 to 10.

2. The composition according to claim 1,
   wherein the at least one sesamin-class compound comprises at least one of sesamin or episesamin.

3. The composition according to claim 1,
   wherein a weight ratio of the PQQ or a salt thereof to the sesamin-class compound (PQQ or a salt thereof/sesamin-class compound) in PQQ equivalent is 0.2 to 5.

4. The composition according to claim 1,
   wherein the composition improves or maintains mitochondrial function or reduces a decline in mitochondrial function.

5. The composition according to claim 1,
   wherein the composition improves or maintains mitochondrial energy production capacity or reduces a decline in mitochondrial energy production capacity.

6. The composition according to claim 1,
   wherein the composition is for use in improving or maintaining vitality or reducing a decline in vitality.

7. The composition according to claim 1,
   wherein the composition is an anti-fatigue composition.

8. The composition according to claim 1,
   wherein the composition is an oral composition.

9. The composition according to claim 1,
   wherein the composition is a food or beverage.

10. A method of improving or maintaining at least one of mitochondrial function or mitochondrial energy production capacity or reducing a decline in at least one of mitochondrial function or mitochondrial energy production capacity, the method comprising:
    administering at least one sesamin-class compound and pyrroloquinoline quinone (PQQ) or a salt thereof such that a weight ratio of the PQQ or a salt thereof to the sesamin-class compound (PQQ or a salt thereof/sesamin-class compound) in PQQ equivalent is 0.1 to 10.

11. A method of reducing, alleviating, or ameliorating fatigue, the method comprising:
    administering at least one sesamin-class compound and pyrroloquinoline quinone (PQQ) or a salt thereof such that a weight ratio of the PQQ or a salt thereof to the sesamin-class compound (PQQ or a salt thereof/sesamin-class compound) in PQQ equivalent is 0.1 to 10.

* * * * *